(12) United States Patent
Pawlowski

(10) Patent No.: US 10,379,131 B2
(45) Date of Patent: Aug. 13, 2019

(54) SYSTEMS AND METHODS FOR DETECTING A LIQUID LEVEL

(71) Applicant: ELBIT SYSTEMS OF AMERICA / KMC SYSTEMS, INC., Fort Worth, TX (US)

(72) Inventor: Frank Pawlowski, Amherst, NH (US)

(73) Assignee: Elbit Systems of America/KMC Systems, Inc., Merrimack, NH (US)

(*) Notice: Subject to any disclaimer, the term of this patent is extended or adjusted under 35 U.S.C. 154(b) by 94 days.

(21) Appl. No.: 15/352,281

(22) Filed: Nov. 15, 2016

(65) Prior Publication Data

US 2017/0138976 A1 May 18, 2017

Related U.S. Application Data

(60) Provisional application No. 62/257,073, filed on Nov. 18, 2015.

(51) Int. Cl.
*G01N 35/10* (2006.01)

(52) U.S. Cl.
CPC . *G01N 35/1016* (2013.01); *G01N 2035/1018* (2013.01); *G01N 2035/1025* (2013.01); *G01N 2035/1034* (2013.01)

(58) Field of Classification Search
CPC ....... G01N 35/1016; G01N 2035/1018; G01N 2035/1025; G01N 2035/1034
See application file for complete search history.

(56) References Cited

U.S. PATENT DOCUMENTS

| | | | |
|---|---|---|---|
| 4,326,851 A | 4/1982 | Bello et al. | |
| 5,365,783 A | 11/1994 | Zweifel | |
| 5,627,522 A | 5/1997 | Walker et al. | |
| 5,855,851 A | 1/1999 | Matsubara et al. | |
| 6,121,049 A * | 9/2000 | Dorenkott | G01N 35/1016 422/108 |
| 6,192,752 B1 | 2/2001 | Blaine | |
| 6,521,187 B1 * | 2/2003 | Papen | B01L 3/0268 222/263 |
| 6,604,054 B2 | 8/2003 | Lipscomb et al. | |
| 6,658,946 B2 | 12/2003 | Lipscomb et al. | |
| 6,663,353 B2 | 12/2003 | Lipscomb et al. | |
| 6,802,205 B2 | 10/2004 | Barguirdjian et al. | |
| 7,150,190 B2 | 12/2006 | Krufka et al. | |
| 7,191,647 B2 | 3/2007 | Harazin et al. | |
| 7,296,461 B2 | 11/2007 | Barguirdjian et al. | |
| 7,387,023 B2 | 6/2008 | Harazin et al. | |
| 7,396,512 B2 * | 7/2008 | DiTrolio | B01L 3/021 422/522 |
| 7,479,391 B2 * | 1/2009 | Bjornson | G01N 35/1009 422/417 |

(Continued)

*Primary Examiner* — Marrit Eyassu
(74) *Attorney, Agent, or Firm* — Conley Rose, P.C.

(57) ABSTRACT

A method for detecting a liquid surface of a liquid sample with a pipetting tip, the method includes receiving an indication of a capacitance of the pipetting tip, and determining, based on a rate of change of the indication of the capacitance rising above a first preselected threshold, that the pipetting tip has come into contact with the liquid surface. The method also includes determining, based on the rate of change of the indication of the capacitance falling below a second preselected threshold, that the pipetting tip has lost contact with the liquid surface.

6 Claims, 8 Drawing Sheets

(56) References Cited

U.S. PATENT DOCUMENTS

| | | |
|---|---|---|
| 7,603,899 B2 | 10/2009 | Li et al. |
| 7,650,785 B1 | 1/2010 | Miskell et al. |
| 7,836,763 B2 | 11/2010 | Harazin et al. |
| 7,964,160 B2 | 6/2011 | Zuppiger et al. |
| 8,057,759 B2 | 11/2011 | Lee et al. |
| 8,225,654 B2 | 7/2012 | Muerset |
| 8,287,806 B2 | 10/2012 | Bjornson et al. |
| 8,357,544 B2 | 1/2013 | Ingenhoven et al. |
| 8,551,788 B2 | 10/2013 | Ingenhoven et al. |
| 8,622,713 B2 | 1/2014 | Hampton |
| 8,807,957 B2 | 8/2014 | Hampton |
| 9,335,200 B2 | 5/2016 | Cors et al. |
| 2001/0047692 A1* | 12/2001 | Lipscomb .......... G01N 35/1009 73/864.25 |
| 2004/0149015 A1* | 8/2004 | Hansen ................ B01L 3/0275 73/40 |
| 2009/0211380 A1* | 8/2009 | Tajima ............... G01N 35/1016 73/864.11 |
| 2009/0235737 A1 | 9/2009 | Lavon et al. |
| 2009/0266149 A1* | 10/2009 | Kaplit ................ G01N 35/1016 73/54.09 |
| 2012/0202238 A1* | 8/2012 | Hyde .................. G01N 15/042 435/29 |
| 2013/0183660 A1 | 7/2013 | Yu et al. |
| 2013/0316329 A1 | 11/2013 | Yu et al. |
| 2014/0007676 A1 | 1/2014 | Armstrong et al. |
| 2014/0017670 A1 | 1/2014 | Yu et al. |
| 2016/0025546 A1 | 1/2016 | Ott et al. |

* cited by examiner

SYSTEMS AND METHODS FOR DETECTING A LIQUID LEVEL

CROSS-REFERENCE TO RELATED APPLICATIONS

This application is related to and claims the benefit of U.S. Provisional Patent Application Ser. No. 62/257,073 filed 18 Nov. 2015 titled "Systems and Methods for Detecting a Liquid Level", which is hereby incorporated by reference as if fully set forth herein.

BACKGROUND

Processing of liquids, such as aspiration and dispensation, is carried out in a variety of contexts. For example, in a laboratory setting, a robotic device may aspirate and dispense liquids using a positive-displacement pump and associated pipette tip in order to carry out a variety of laboratory tasks, such as titration for performing a DNA assay. In such settings, it may be advantageous to detect when the pipette tip comes into and out of contact with the liquid being aspirated or dispensed. However, conventional liquid level detection methods and apparatuses suffer from a lack of sensitivity, which can result in inaccuracies when aspirating and dispensing small volumes (e.g., microliters) of liquid, a poor ability to accurately confirm whether the pipette tip has fallen out of the liquid during aspiration, and/or a poor ability to confirm that the proper downward motion of the pipette tip has occurred to compensate for a height reduction of a liquid sample resulting from a previous aspiration.

BRIEF DESCRIPTION OF THE DRAWINGS

For a detailed description of exemplary embodiments of the disclosure, reference will now be made to the accompanying drawings in which.

NOTATION AND NOMENCLATURE

Figure 1:
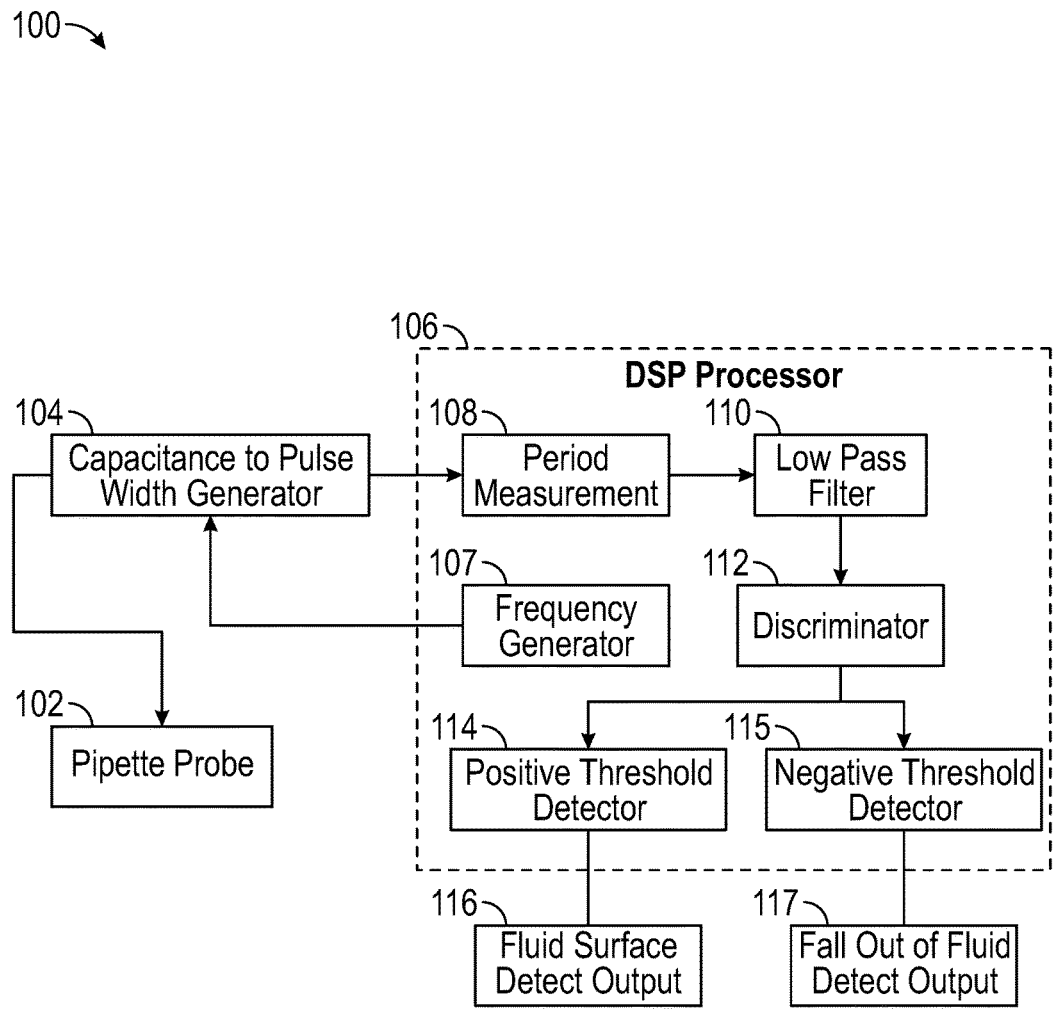
FIG. 1 shows a block diagram of a system to detect a liquid surface using a capacitance-based measurement and determination in accordance with various embodiments of the present disclosure.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

The following discussion is directed to various embodiments of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As explained above, conventional liquid level detection methods and apparatuses suffer from a lack of sensitivity, which results in less than ideal performance in a number of scenarios. One reason for the lack of sensitivity stems from designs that rely heavily on analog signal processing for detecting and processing various signals related to liquid level sensing, such as capacitance and pressure or vacuum. Embodiments of the present disclosure address these and other shortcomings, resulting in a systems and methods for detecting a liquid level that are more accurate, capable of resolving anomalies in the pipetting process (e.g., clotting, bubble formation, foaming, and the like), and generally more robust in laboratory environments where variables such as container size, liquid type, and other parameters may change over time and without being known to the associated liquid processing hardware and software.

This disclosure is generally directed to methods for detecting a liquid surface of a liquid sample with a pipetting tip coupled to a positive displacement pump. Certain examples utilize capacitance-based determinations, while other examples utilize pressure (or vacuum)-based determinations. Generally, examples of the present disclosure will be described with reference to a pump mounted to a robotic arm controlled by associated control hardware and/or software. However, it should be appreciated that liquid level detection methods disclosed herein may be applicable in a variety of fields outside of laboratory robotics.

For capacitance-based determinations, the pipetting tip is conductive and is part of a circuit that measures capacitance. When the pipetting tip contacts a liquid in a container (e.g., a microtiter plate), a near-instantaneous increase in the capacitance is observed, which may be processed to determine a position of the liquid surface in relation to the range of motion of the robotic arm supporting the pump, for example.

Similarly, when the pipetting tip is drawn out of the liquid (or when the liquid level falls below the pipetting tip due to the downward motion of the robotic arm being insufficient to maintain contact with the liquid), a near-instantaneous decrease in the capacitance is observed, which may be processed to determine a position or an updated position of the liquid surface in relation to the range of motion of the robotic arm. Further, in certain contexts, a determination that the pipetting tip has lost contact with the liquid when it was not expected to do so may result in a change in one or more operational parameters of the robotic control or pump control systems, which will be explained in further detail below.

For pressure-based determinations, a pressure transducer is coupled to the working airspace of the pump (e.g., a cylinder whose volume changes as a result of displacement of a piston into and out of the cylinder) to detect a pressure of the airspace, which is coupled to the airspace in the pipetting tip. As the pipetting tip is moved toward a liquid surface, the pump controller causes the pump to begin aspirating air, resulting in a slight vacuum in the pipetting tip and associated airspace, which is detected by the pressure transducer. When the pipetting tip contacts a liquid in a container (e.g., a microtiter plate), a near-instantaneous increase in the vacuum (or a corresponding decrease in measured pressure) is observed, which may be processed to determine a position of the liquid surface in relation to the range of motion of the robotic arm supporting the pump, for example. Although a volume of liquid may be aspirated before the vacuum change is detected, in many applications the volume may be quite minimal (e.g., several microliters) and thus insignificant to an overall sample volume to be collected.

Similarly, when the pipetting tip is drawn out of the liquid (or when the liquid level falls below the pipetting tip due to the downward motion of the robotic arm being insufficient to maintain contact with the liquid), a near-instantaneous decrease in vacuum (or a corresponding increase in measured pressure, resulting from the inflow of atmospheric pressure air to the airspace) is observed, which may be processed to determine a position or an updated position of the liquid surface in relation to the range of motion of the robotic arm. Further, in certain contexts, a determination that the pipetting tip has fallen out of contact with the liquid when it was not expected to do so may result in a change in one or more operational parameters of the robotic control or pump control systems, which will be explained in further detail below.

In both capacitance- and pressure-based determinations, a rate of change of the capacitance and pressure may be compared to a threshold rate of change to determine whether a liquid surface has been contacted. That is, a rate of change in pressure or capacitance above the threshold corresponds to contacting the liquid surface, while a rate of change in pressure or capacitance below the threshold may correspond to an anomalous measurement, a measurement influenced by an external, non-liquid surface-related factor (e.g., capacitance of nearby bodies influencing the capacitance seen at the pipetting tip, and the like. A similar rate of change-based analysis may be performed to detect the pipetting tip no longer contacting the liquid, where a rate of change below a negative threshold indicates that the pipetting tip has fallen out of contact with the liquid surface.

Turning now to FIG. 1, a system 100 to detect a liquid surface using a capacitance-based measurement and determination is shown in accordance with various embodiments. The system 100 includes a probe 102, such as a pipette tip; however, in certain embodiments a capacitively-coupled probe 102 may be used in conjunction with a traditional pipette tip, which is not shown for simplicity. The probe 102 is a conductive probe that is isolated from ground, and is attached to a circuit that measures capacitance seen by the probe 102 as explained in further detail below.

A capacitance to pulse width generator 104 logic block generates a pulse having a width related to the value of capacitance sensed from the probe 102. That is, the pulse width generator 104 generates a pulse whose time duration is proportional to the capacitance measured by the probe 102. Stated otherwise, a capacitance to pulse width generator 104 is configured to output a pulse having a width based on a capacitance seen by the pipette probe. As will be explained in further detail below, in certain embodiments of the present disclosure an absolute capacitance value is not particularly important, but rather a determination is made based on a perceived rate of change of the capacitance value indicated by the pulse generated by the pulse width generator 104. In certain other embodiments, the system 100 may be calibrated such that the absolute value of capacitance sensed from the probe 102 and indicated by the pulse width generator 104 is leveraged instead of or in addition to the rate of change of capacitance in order to provide further accuracy in detecting a liquid surface.

The output of the pulse width generator 104 is provided to a digital signal processor (DSP) 106 and, in particular, a period measurement block 108 of the DSP 106. DSP 106 is configured to compare a signal based on the width of the pulse with a preselected positive threshold and a preselected negative threshold, as described further below. In at least some embodiments, the period measurement block 108 gates an oscillator (not shown) of the DSP 106 in response to receiving a pulse from the pulse width generator 104 and counts the number of oscillator cycles that occur during the duration of receiving the pulse from the pulse width generator 104. The number of oscillator cycles counted indicates a relative value of capacitance or, in embodiments where the system is so calibrated, may indicate an absolute value of capacitance seen by the probe 102.

The DSP 106 also includes a frequency generator 107, which may divide down the oscillator signal generated by the DSP 106 (e.g., a 30-60 MHz signal) to a frequency more appropriate for the capacitance to pulse width generator 104 (e.g., 40 kHz). The signal provided by the frequency generator 107 is used to trigger a oneshot in the pulse width generator 104. An output period of the oneshot varies as a function of the capacitance of the probe 102 and whatever the probe 102 is in contact with. As described above, the output period of the oneshot is measured by the gated timer of the period measurement block 108. Stated otherwise, the output period of a capacitance to pulse width generator 104 is based on the capacitance seen by the pipette probe, and the period measurement block 108 is configured to measure the output period of the a capacitance to pulse width generator.

The DSP 106 also includes a low pass filter 110 that receives the "count" or indication of pulse duration from the period measurement block 108. In certain embodiments, the low pass filter 110 may comprise a $3^{rd}$-order infinite impulse response (IIR) filter. The filter 110 reduces noise components of the signal generated by the period measurement block 108. In particular, because the values of capacitance being sensed by the probe 102 may be very small, the signal output by the period measurement block 108 may include large amounts of high-frequency noise (i.e., the signal-to-noise ratio (SNR) of the output of block 108 may be expected to be poor). Thus, the filter 110 reduces the high-frequency noise generated by block 108 to produce a relatively clean, noise-reduced signal.

Figure 2:
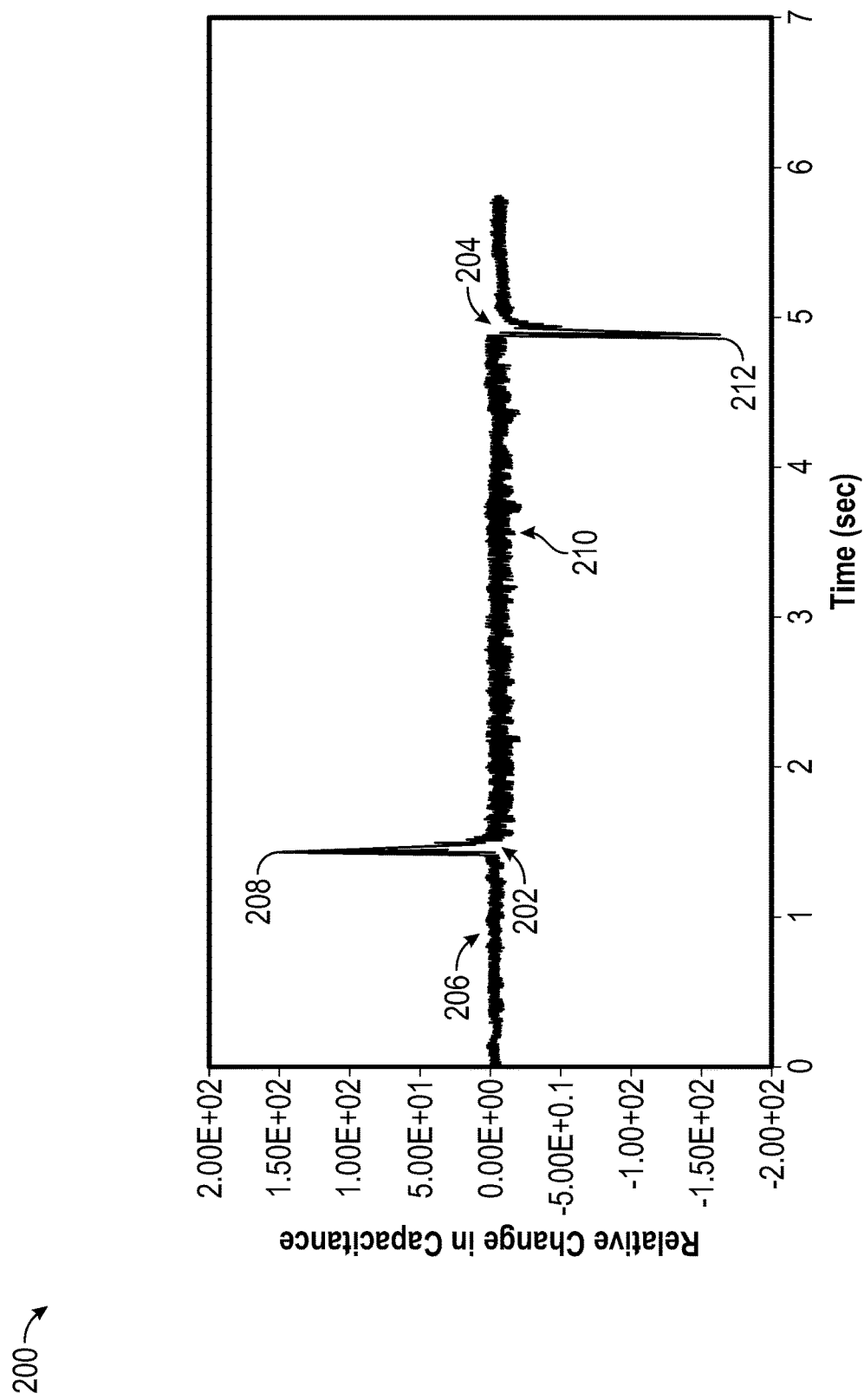
FIG. 2 shows an exemplary change in capacitance curve as a function of time to illustrate the function of the system of FIG. 1 in accordance with various embodiments of the present disclosure.

The noise-reduced output of the filter 110 is provided to a discriminator block 112, which identifies sudden positive or negative slope changes (i.e., rates of change above or below certain, preselected thresholds). Stated otherwise, a discriminator 112 may be configured to identify a change in slope in the signal based on the width of the pulse from a capacitance to pulse width generator 104 and generate a signal having a magnitude based on the change in slope. In some embodiments, the discriminator block 112 may comprise a 20$^{th}$ order finite impulse response (FIR) filter, which discriminates the sudden changes from a background signal. When the probe 102 contacts a liquid surface, a large pulse is generated by the low pass filter 110 and discriminator 112. Conversely, when the probe 102 falls out of contact with a liquid, a similarly-large but opposite-sign pulse is generated by the low pass filter 110 and discriminator 112 (FIG. 2).

The DSP 106 may compare a magnitude of the pulse generated by the discriminator 112 to a threshold 114, 115 to determine whether the pulse is to be interpreted as contacting (or losing contact with) a liquid surface. In other words, a positive threshold detector 114 may compare the magnitude of the signal from a discriminator 112 having a positive sign with the preselected positive threshold, and a negative threshold detector 115 may compare the magnitude of the signal from a discriminator 112 having a negative sign with the preselected negative threshold. In other embodiments, the DSP 106 may compare a rate of change of the pulse generated by the discriminator 112 to a threshold to determine whether the rate of change of the pulse is to be interpreted as contacting (or losing contact with) a liquid surface. Advantageously, the threshold may be set at a point between the peak value of the noise (La, so noise present in the discriminator 112 output does not trigger a detection) and the peak value of the discriminator 112 output when contacting (or losing contact with) a liquid surface.

In certain embodiments, the DSP 106 may "stretch" the threshold detector 114, 115 output(s) after comparing it to a threshold to avoid potential difficulties associated with identifying a very narrow (i.e., transient) signal pulse for subsequent use as to whether the probe 102 has contacted or fallen out of contact with a liquid surface. It should be appreciated that various ones of the described components of the system 100 may have their circuitry and/or component values adjusted to provide appropriate resolution and dynamic range for the particular system 100 requirements and operating environment context.

Ultimately, detected outputs 116, 117, which may indicate whether the probe 102 has contacted or fallen out of contact with a liquid surface, may be provided to various other control circuitry or mechanisms, including hardware, software, and/or combinations thereof. These control mechanisms will be described in further detail below. Further, it should be appreciated that although the detected outputs 116, 117 are shown as separate outputs, the actual output of the DSP 106 may comprise a serial data output that indicates both of the detected outputs 116, 117.

FIG. 2 shows an example graph 200 of relative change in capacitance (in arbitrary units) as a function of time. A response 202 (i.e., a pulse generated by the discriminator 112) occurs when the pipetting tip 102 contacts a liquid surface. Similarly, a response 204 (i.e., an opposite-sign pulse generated by the discriminator 112) reflects the change in capacitance reaction when the pipetting tip 102 comes out of contact with the liquid surface. It is noted that noise components of the output of the discriminator 112 become worse between pulses 202, 204 because capacitance sensed while the probe 102 is in the liquid is a larger value, and thus more variation is introduced into the signals input to the discriminator 112. Noise regions 206 and 210, and the positive and negative peak values 208, 212 of pulses 202 and 204 respectively are described further in conjunction with FIG. 8.

Figure 3:
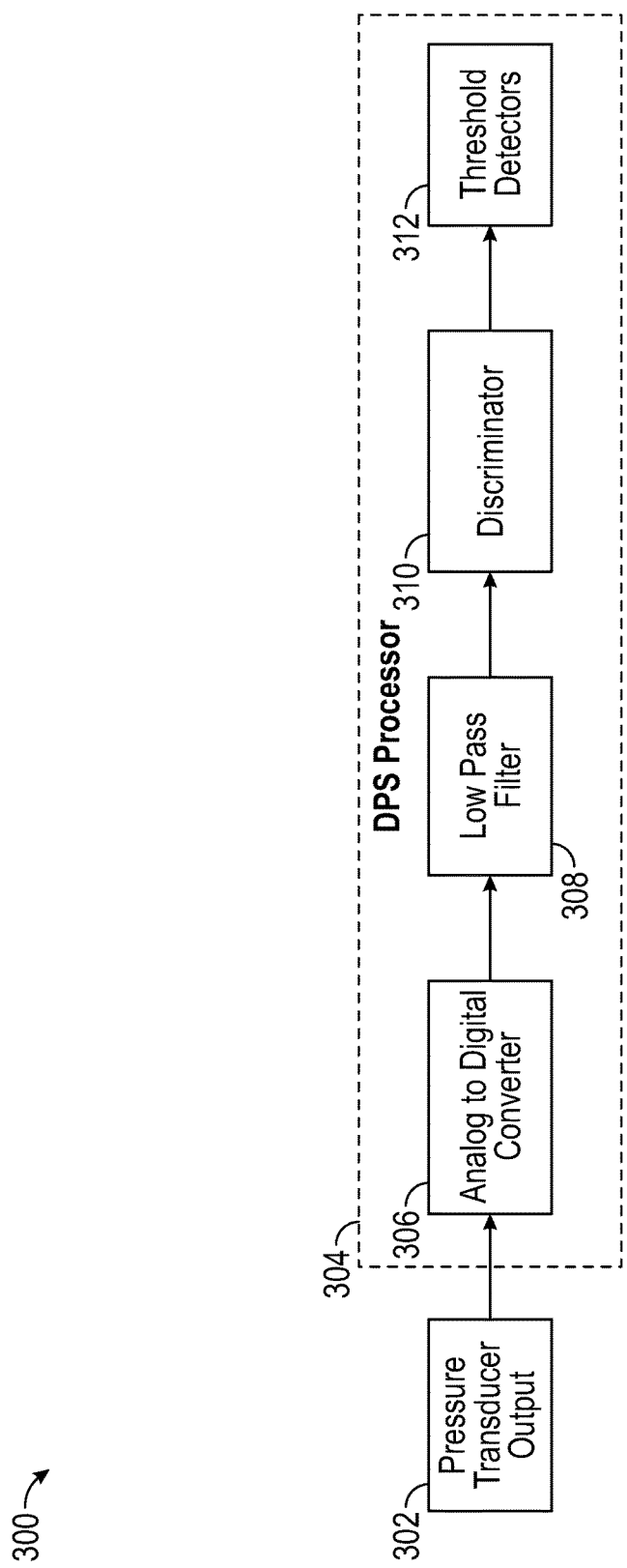
FIG. 3 shows a block diagram of a system to detect a liquid surface using a pressure-based measurement and determination in accordance with various embodiments of the present disclosure.

Turning now to FIG. 3, a system 300 to detect a liquid surface using a pressure-based measurement and determination is shown in accordance with various embodiments.

The system 300 is generally similar to the system 100 that relies upon a capacitance-based measurement and determination. Of course, rather than a conductive probe 102, the system 300 includes a pressure transducer 302. The pressure transducer 302 generates an output signal related to a pressure values (or vacuum value) sensed by the pressure transducer 302. The pressure transducer 302 may be positioned in fluid communication with a working airspace of a pump, such as a pump cylinder, which is also in fluid communication with the interior volume of a pipette tip when coupled to the pump. Advantages may be realized by reducing the total volume of air the pressure transducer 302 is in communication with, which may result in an increase in precision and/or accuracy of the signal generated by the pressure transducer 302.

The system 300 includes a DSP 304 similar to the system 100 described above in FIG. 1. The pressure transducer 302 may be coupled to the DSP 304 wherein the DSP 104 may be configured to output a signal having an amplitude based on a rate of change of a pressure in the interior volume of the pipette tip, as described further below. The DSP 304 includes an analog-to-digital converter (ADC) 304, a low pass filter 308, and a discriminator 310 and detectors 312, which are similar in function to their counterparts described above with regard to FIG. 1. In at least some embodiments, the discriminator 310 may be coupled to an output of an ADC 304 via a low pass filter 308, and be configured to output a signal having a magnitude based on a magnitude of the rate of change of the pressure in the interior volume of the pipette tip. The output signal of the discriminator 310 may have a sign based on the sign of the rate of change of the pressure in the interior volume, e.g. a positive signal for a positive rate of change, and vice versa. Similar to threshold detectors 114, 115, FIG. 1, the output signal of the discriminator 310 may be coupled to detectors 312, wherein the detectors 312 are configured to compare the output signal of the discriminator 310 having a positive sign with a preselected positive threshold and the output signal having a negative sign with a preselected negative threshold.

As will be appreciated, a pressure-based determination as in FIG. 3 is better suited for use while actively pipetting (i.e., operating the pump to aspirate or dispense from the pipette tip, even if only air). For example, when contacting a liquid surface while aspirating through the pipette tip, an increased change in pressure detected (and thus a more appreciable rate of change of pressure) is observed, which results in easier subsequent detection. However, capacitance-based determinations are not reliant on whether pipetting is occurring, and thus may be utilized in a potentially-wider variety of contexts. Pressure-based determinations have the advantage of not requiring a conductive pipetting tip, however.

Further, pressure-based determinations may provide advantages over capacitive-based determinations when detecting foam or clotting conditions, which capacitance does not effectively discriminate against. For example if foam is on the surface of sample is contacted by the capacitance probe, it cannot effectively differentiate that contact from contacting the surface. In the case of pressure, if during aspiration there is foam on the surface of the liquid sample there will be sudden changes in pressure while trying to aspirate the foam that can be used to indicate that the sample has foam on its surface and accurate pipetting may not be possible. Similarly, if during aspiration a clot is aspirated and it blocks flow in the tip, vacuum will increase by more than an expected, or predetermined, amount and a clogged pipetter condition can be detected.

Further, in certain embodiments, knowledge of properties of the liquid being aspirated may be leveraged to improve clotting and/or foam detection. For example, the system 300 may be improved by utilizing knowledge regarding liquid viscosity, density, and the like and possibly applying different sets of parameters and/or thresholds for each various liquid being handled. In other embodiments, an expected pressure value may be correlated to a rate of aspiration (e.g., using a lookup table or equation) such that if an observed pressure deviates from an expected, or predetermined, pressure for a given rate of aspiration, then foaming, clotting, short sampling, or other anomalous condition may be detected. The lookup table or equation may also take into account the pipette tip inner diameter, which varies by pipette size (volume).

Figure 4:
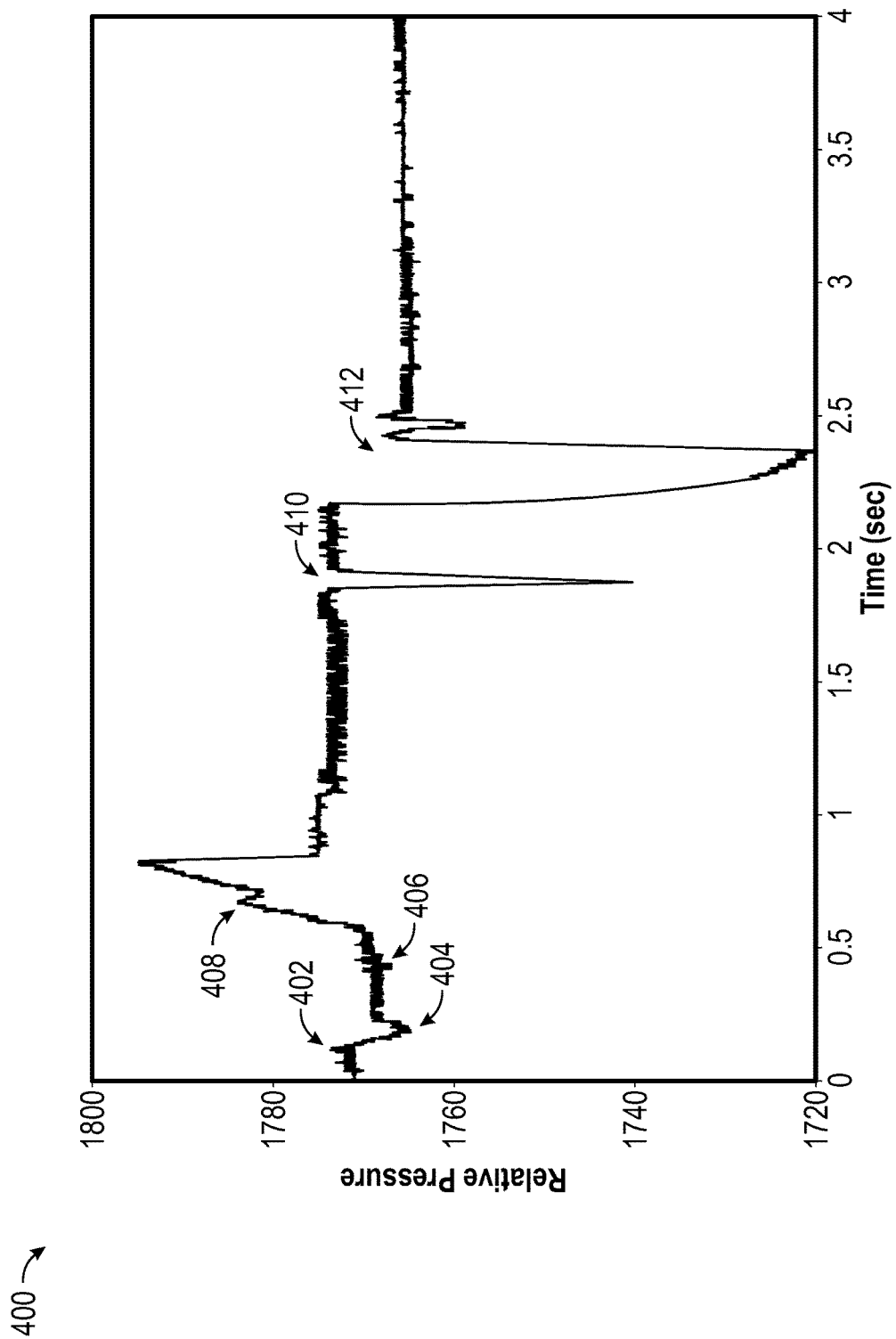
FIGS. 4 and 5 show exemplary pressure curves as a function of time to illustrate the function of the system of FIG. 3 in accordance with various embodiments of the present disclosure.

FIG. 4 shows an exemplary relative pressure (in arbitrary units) curve 400 as a function of time, which demonstrates various events that may be detected using a pressure-based determination, explained above. The following discussion refers to aspects of the pressure curve 400 in chronological order.

The pressure curve 400 includes signal 402 where the liquid surface is contacted as the pipetter is moved toward the surface while the pipetter is aspirating. The pressure curve 400 also includes a time at which a pre-selected vacuum threshold 404 is set. At this time, the relative location of the surface is established by noting the position of the pipetter at that time and the aspiration stops.

Subsequently, the pressure curve 400, at 406, reflects the pipette tip 102, FIG. 1, coming out of contact with the liquid. The pressure curve 400 trends upward at 408 while dispensing liquid and air aspirated during the liquid level detecting operation. Then, as an air gap is aspirated to allow subsequent full dispensing of the sample volume, the pressure curve 400 falls sharply, at 410, due to a vacuum being pulled in the working airspace of the pump. Finally, when aspirating a liquid sample, the vacuum pulled is even sharper, resulting in a more pronounced decrease in the pressure curve 400, at 412.

Figure 5:
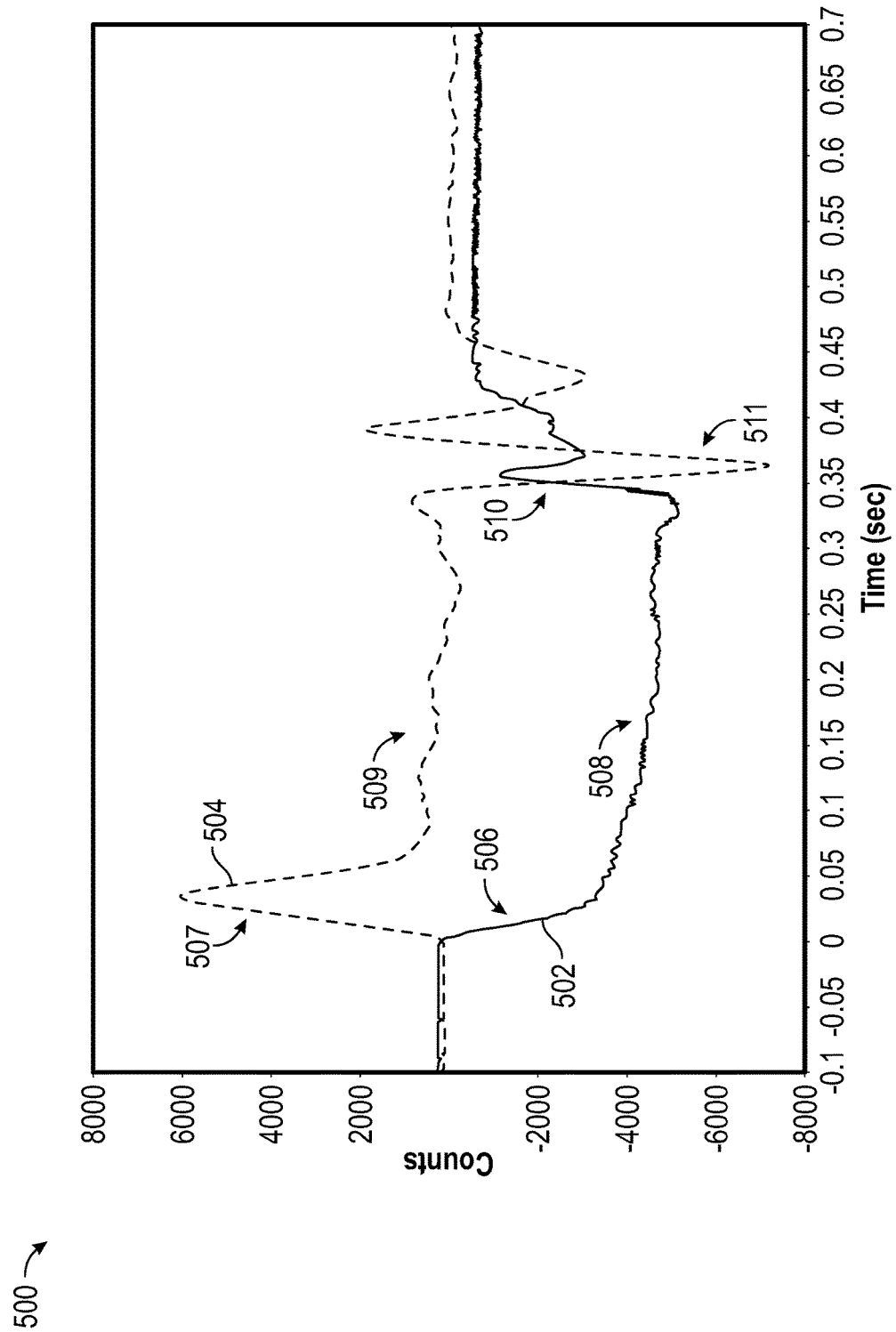

FIG. 5 shows an exemplary graph 500 demonstrating pressure readings as well as a rate of change of vacuum as a function of time, which particularly represents the identification of a short sample using a pressure-based determination. Curve 502 (solid line) on the graph 500 shows the relative pressure (in counts, on the vertical axis) versus time (on the horizontal axis) during aspiration of a sample with pipetter robot speed reduced to force a short aspiration or sample (La, where the pipette tip loses contact with the liquid during aspiration). The rate of change of the vacuum is plotted in curve 504 (dashed line). Thus a decrease in pressure is an increase in vacuum and thus corresponds to a positive rate-of-change of vacuum, and vice versa. In this example graph 500, the desired aspiration time is 0.4 seconds. The pressure initially reduces rapidly, at 506, and then more gradually, at 508, until the pipette tip pulls out from the liquid, at approximately 0.35 seconds. These correspond to regions 507 and 509 in curve 504. At this time the pressure rises rapidly, region 510 in curve 502, corresponding to dip 511 in curve 504, and can be used to determine that an incomplete aspiration has occurred, as the full desired aspiration time of 0.4 seconds was not reached before it is determined that the pipette tip lost contact with the liquid. Similarly the rate of change of vacuum can be used to make this determination by comparing the value in the dip 511 to a predetermined threshold.

Certain embodiments of the present disclosure may use both pressure-based and capacitance-based determinations in tandem, in order to provide advantages associated with each type of determination. Further, as indicated above, a detected output 116, 117 may indicate whether the probe 102 has contacted or fallen out of contact with a liquid surface. Subsequent control mechanisms may incorporate various algorithms to detect and address issues associated with different container or vessel sizes.

For example, in the event a system 100, 300 has been incorrectly programmed to work with a certain container size in a particular fluid processing step, embodiments of the present disclosure may identify the incorrect container size and cause the control mechanisms to update a container size. For example, if it is determined that the pipette tip has fallen out of a liquid before it should have (e.g., the robotic arm is not moving down fast enough for the rate of aspiration due to an underestimation of container size), or that the pipette tip remains in contact with the liquid when it should have fallen out (e.g., the robotic arm is not moving up as expected).

In either of these examples, the control mechanisms may update one or more parameters associated with that particular step of the fluid processing, such as adjusting the container size, adjusting the rate of movement of the robotic arm during aspiration, and/or adjusting the rate of aspiration of the pump itself. Depending on the time available, and in the event of a short sample, the short sample may either be dispensed and a second aspiration attempt made (either with or without altering parameters of that fluid processing step as described above) or a test associated with that particular sample may be identified as deficient (e.g., the sample and the remainder of the fluid processing of that sample is thrown away).

To ease calibration of the system 100, 300, a normal and short aspiration cycle may be carried out while monitoring the level of output from the discriminator 112, for example. Based on the output from the discriminator during these cycles, signal processing parameters such as optimum thresholds (e.g., rate of change of capacitance or pressure that corresponds to a known liquid surface contact or loss of contact event) may be determined for subsequent use to detect contact and loss of contact with a liquid surface. In this way, various systems 100, 300 may compensate for slight unit-to-unit sensitivity variation due to manufacturing tolerances, or variations due to working with liquids having different physical characteristics, and the like. This strategy can also be used to optimize performance for different liquid types that need to be aspirated by a pipetter on the same system, for example where certain characteristics differ between liquids used in different stages of the laboratory process.

Embodiments of the present disclosure may also be directed to a non-transitory computer-readable medium. Such a computer-readable medium may contain instructions that, when executed by a processor (e.g., DSP 106, 304, or another microprocessor coupled thereto), cause the processor to carry out all or portions of the methods and processes described herein.

Figure 6:
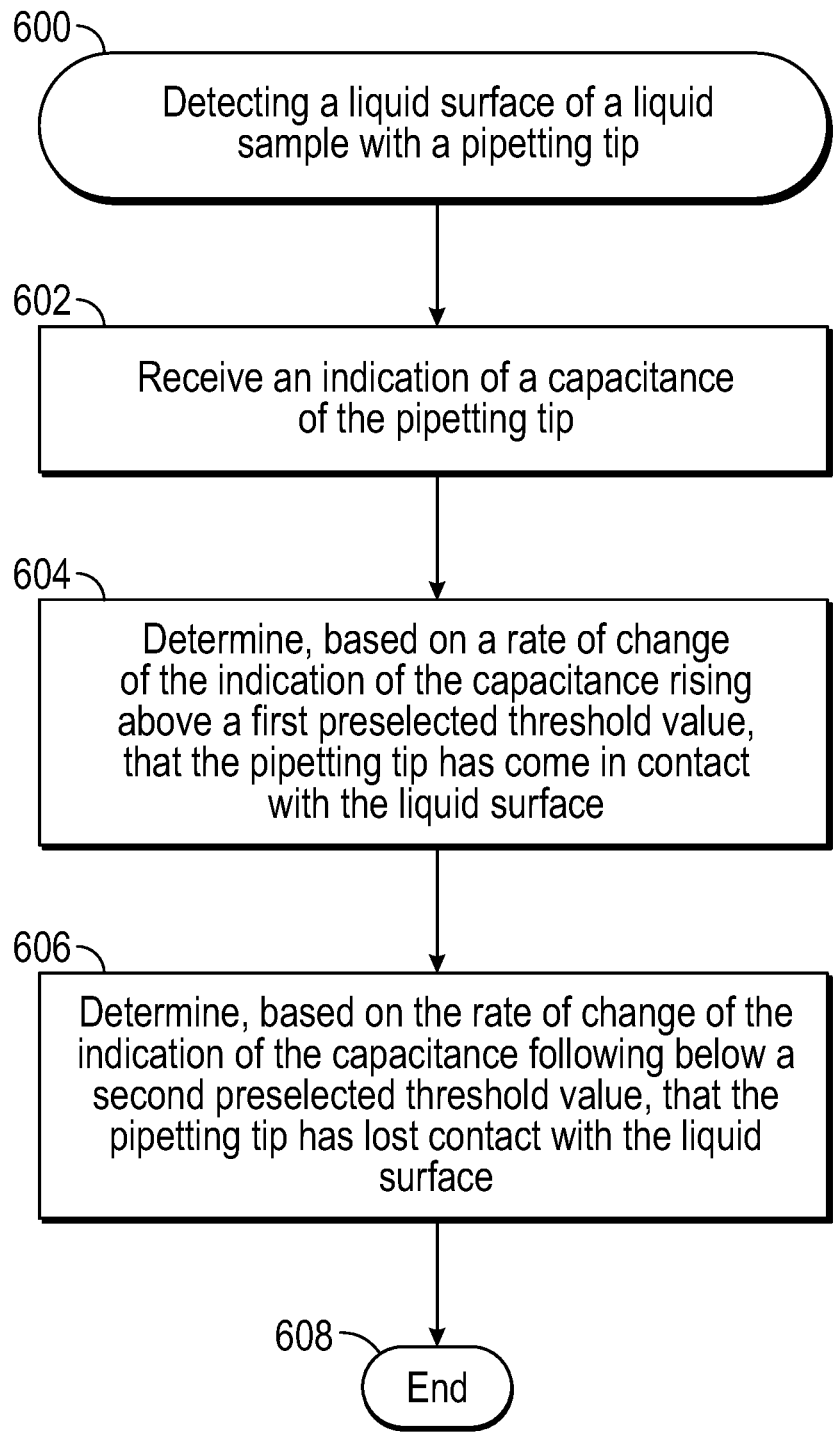
FIG. 6 shows a flow chart of a method in accordance with an embodiment.

Embodiments of the present disclosure provide a method of detecting a liquid surface as part of a pipetting sequence. This minimizes pipette tip wetting and improves precision and accuracy of the pipetting. Further, sensitivity and detection are improved to the point of permitting aspirating and dispensing of volumes in the low microliter range. FIG. 6 shows a flowchart of a method for detecting a liquid surface of a liquid sample with a pipetting tip, block 600. In block an indication of a capacitance of the pipetting tip is received. In block 604 it is determined that the pipetting tip has come in contact with the liquid surface based on the rate of change of the indication of the capacitance rising above a first preselected threshold value. In block 606, it is determined that the pipetting tip has lost contact with the liquid surface based on the indication of the capacitance falling below a second preselected threshold value. Thus In addition to detecting when contact is made with the liquid surface, the method also detects when a pipetting tip or probe has lost contact with the liquid, which may be leveraged to assure that the pipetting tip has not lost contact with the liquid while it is being aspirated, via a positive displacement pump coupled to the pipetting tip, for example (i.e., that a short sample condition has not occurred). Stated otherwise, in response, during aspiration of the liquid sample into the pipetting tip, to determining that the pipette tip has lost contact with the liquid surface prematurely, the liquid sample may be identified as a short sample. In response to identifying the sample as a shot sample, a remedial action may be performed. Exemplary remedial actions include dispensing the short sample and aspirating a second sample. Further example remedial actions comprise dispensing the short sample, altering one or more parameters of positive displacement pump or a motion control apparatus such as a robotic arm coupled to the positive-displacement pump and aspirating a second liquid sample into the pipetting tip using the altered parameters, or alternatively, a test associated with the short sample may be identified as deficient. Note further that this function further provides a confirmation that the proper downward motion of the pipette tip has occurred to compensate for the height reduction of the liquid in the tube as it is being aspirated. Method 600 ends at block 608.

Figure 7:
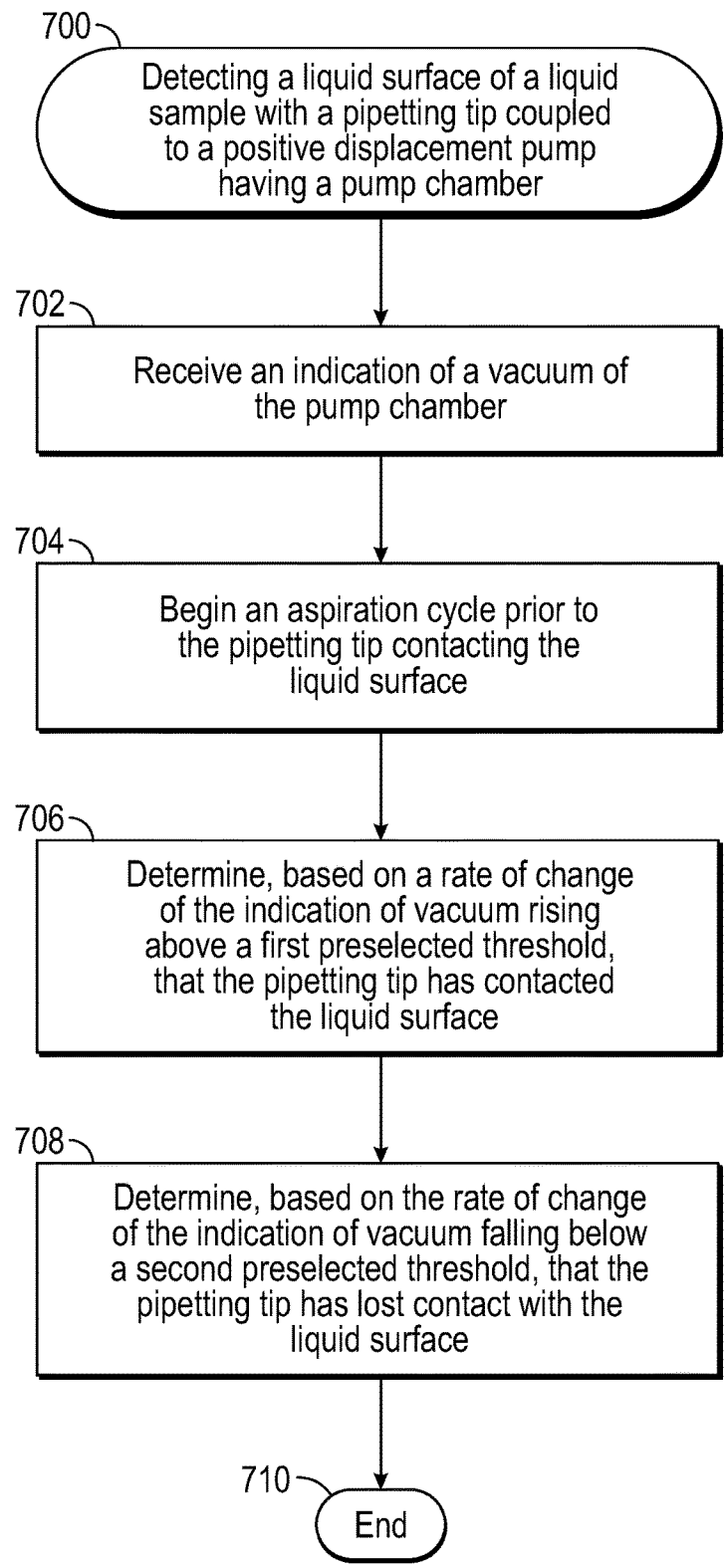
FIG. 7 shows a flowchart of a method in accordance with an embodiment.

FIG. 7 show a flowchart of a method for detecting a liquid surface of a liquid sample, block 700, the detecting with a pipetting tip coupled to a positive displacement pump having a pump chamber. In block 702, an indication of a vacuum of the pump chamber is received. An aspiration cycle is begun prior to the pipetting tip contacting the liquid surface, in block 704. In block 706, it is determined, based on a rate of change of the indication of vacuum rising above a first preselected threshold, that the pipetting tip has contacted the liquid surface. In block 708, it is determined, based on a rate of change of the indication of vacuum falling below a second preselected threshold, that the pipetting tip has lost contact with the liquid surface. Further, during aspiration of the liquid sample, a clotting condition and a foaming condition proximate to the pipetting tip may be identified: the clotting condition may be identified by the indication of vacuum increasing by more than a first predetermined amount. The foaming condition proximate to the pipetting tip may be identified by the indication of vacuum varying in time by more than a second predetermined amount. In response to identifying either the clotting condition or the foaming condition, a remedial action may be performed. Note, as described above, the first and second predetermined amounts may be based on a size of the pipetting tip, and/or rate of aspiration, for example.

Figure 8:
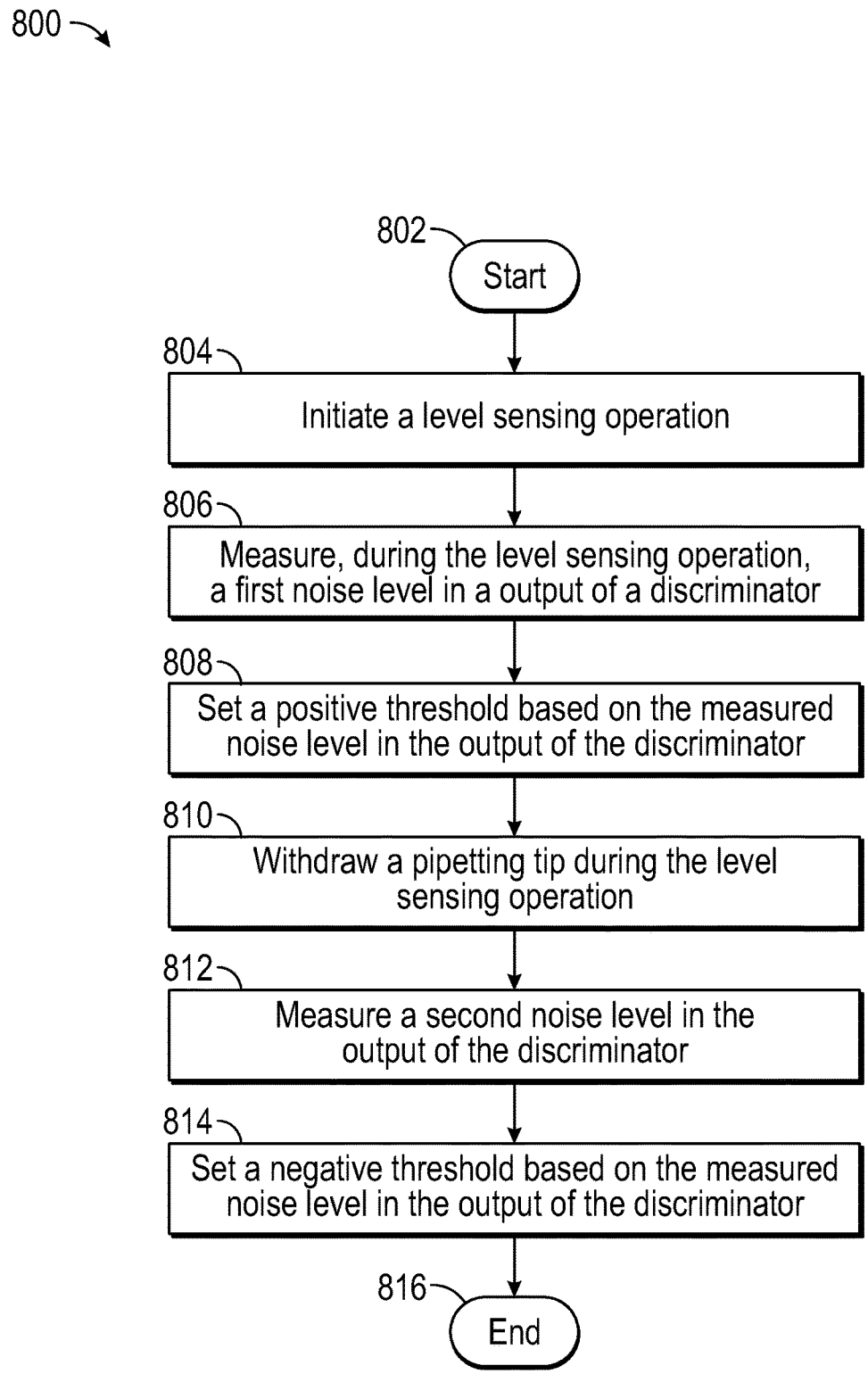
FIG. 8 shows a flowchart of a method in accordance with an embodiment.

As described above, a calibration may be performed to set the thresholds. FIG. 8 shows a flowchart of a method 800 which may be used to set thresholds in accordance with an embodiment. Method 800 starts at block 802. In block 804, a level sensing operation, as previously described, is initiated. During the level sensing operation, as the pipetting probe descends toward the surface of the fluid sample, a first noise level of an output of the discriminator, e.g. discriminator 112, FIG. 1, is measured, in block 806. For example, referring to FIG. 2, in at least some embodiments, a root mean-square (RMS) value of the signal in noise region 206 may be used to establish a positive threshold value at a preselected multiple of the RMS noise, e.g. three times the RMS noise signal, to mitigate against false detection of the contact of the pipette probe with the surface of the fluid sample. In other embodiments, a multiple of the positive peak noise value in the noise region 206 may be used as the preselected positive threshold. In still other embodiments, the positive threshold may be set at the average between the RMS value in region noise region 206 and the detected positive peak value 208 of pulse 202. In still other embodiments, the positive threshold may be set at an average of the peak positive value in the noise region 206 and the detected positive peak value 208 of pulse 202. Further still, in some embodiments, a statistical measurement of the noise may be used, and the positive threshold may be set to a preselected multiple, for example, 5×, of the standard deviation of the first noise level of the output of the discriminator. In block 808, the positive threshold is set based on the measured first noise level in the output of the discriminator, in block 806. The pipetting tip is withdrawn during the level sensing operation, in block 810, and in block 812, a second noise level of the discriminator output signal is measured. For example, the second noise level is measured in noise region 210, FIG. 2. Similar to setting the positive threshold, in at least some embodiments, a root mean-square (RMS) value of the signal in noise region 210 may be used to establish a negative threshold value at a preselected multiple of the RMS noise, e.g. three times the RMS noise signal, to mitigate against false detection of the loss of contact of the pipette probe with the surface of the fluid sample. In other embodiments, a multiple of the negative peak noise value in the second noise level may be used as the preselected negative threshold. In still other embodiments, the negative threshold may be set at an average of the peak negative value in the noise region 210 and the detected negative peak value 212 of pulse 204. In still other embodiments, the negative threshold may be set at the average between the RMS value in region noise region 210 and the detected negative peak value 212 of pulse 204. Further still, in some embodiments, a statistical measurement of the noise may be used, and the negative threshold may be set to a preselected multiple, for example, similar to the positive threshold case, 5×, of the standard deviation of the second noise level of the output of the discriminator. In block 814 the preselected negative threshold is set based on the measurement in block 812. Method 800 ends at block 816.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

What is claimed is:

1. A method for detecting a liquid surface of a liquid sample with a pipetting tip coupled to a positive-displacement pump having a pump chamber, the method comprising:
receiving, by a signal processor coupled to the positive-displacement pump, an indication of a vacuum of the pump chamber;
beginning an aspiration cycle prior to the pipetting tip contacting the liquid surface;
determining, by the signal processor based on a rate of change of the indication of vacuum rising above a first preselected threshold, that the pipetting tip has come into contact with the liquid surface; and determining, by the signal processor based on the rate of change of the indication of vacuum falling below a second preselected threshold, that the pipetting tip has lost contact with the liquid surface.

2. The method of claim 1 further comprising:
during aspiration of the liquid sample, and in response to the indication of the vacuum increasing by more than a predetermined amount, identifying a clotting condition in the pipetting tip; and
in response to identifying the clotting condition, performing a remedial action.

3. The method of claim 1 further comprising:
during aspiration of the liquid sample, and in response to the indication of the vacuum varying in time by more than a predetermined amount, identifying a foaming condition proximate to the pipetting tip; and
in response to identifying the foaming condition, performing a remedial action.

4. A system for detecting a liquid surface of a liquid sample comprising:
a positive-displacement pump having a pump chamber;
a pipetting tip coupled to the positive-displacement pump; and
a signal processor coupled to the positive-displacement pump, the signal processor configured to:
receive an indication of a vacuum of the pump chamber;
begin an aspiration cycle prior to the pipetting tip contacting the liquid surface;
determine, based on a rate of change of the indication of vacuum rising above a first preselected threshold, that the pipetting tip has come into contact with the liquid surface; and
determine, based on the rate of change of the indication of vacuum falling below a second preselected threshold, that the pipetting tip has lost contact with the liquid surface.

5. The system of claim 4, wherein the signal processor is further configured to:
during aspiration of the liquid sample, and in response to the indication of the vacuum increasing by more than a predetermined amount, identify a clotting condition in the pipetting tip; and
in response to identifying the clotting condition, perform a remedial action.

6. The system of claim 4, wherein the signal processor is further configured to:
during aspiration of the liquid sample, and in response to the indication of the vacuum varying in time by more than a predetermined amount, identify a foaming condition proximate to the pipetting tip; and
in response to identifying the foaming condition, perform a remedial action.

* * * * *